United States Patent [19]
Uto et al.

[11] Patent Number: 5,135,303
[45] Date of Patent: Aug. 4, 1992

[54] METHOD OF AND APPARATUS FOR INSPECTING SURFACE DEFECTS

[75] Inventors: Sachio Uto; Yoshimasa Ohshima, both of Yokohama, Japan

[73] Assignee: Hitachi, Ltd., Tokyo, Japan

[21] Appl. No.: 658,258

[22] Filed: Feb. 20, 1991

[30] Foreign Application Priority Data

Feb. 20, 1990 [JP] Japan .................................... 2-37371

[51] Int. Cl.⁵ ............................................. G01N 21/89
[52] U.S. Cl. ...................................... 356/237; 250/563
[58] Field of Search .......................... 356/237; 250/563

[56] References Cited

U.S. PATENT DOCUMENTS

| | | | |
|---|---|---|---|
| 3,920,970 | 11/1975 | Slaker | 356/237 |
| 4,626,101 | 12/1986 | Ogawa et al. | 356/237 |
| 4,674,875 | 6/1987 | Koizumi | 356/237 |
| 4,768,878 | 9/1988 | Heine et al. | 356/237 |
| 4,954,723 | 9/1990 | Takahashi et al. | 356/237 |

FOREIGN PATENT DOCUMENTS 208408 11/1984 Japan ..................................... 356/237

*Primary Examiner*—Richard A. Rosenberger
*Attorney, Agent, or Firm*—Antonelli, Terry, Stout & Kraus

[57] ABSTRACT

The present invention relates to a method of inspecting a defect on a surface of a test piece, and to an apparatus using this method. The method comprises the steps of dividing the surface of the test piece into a plurality of inspection regions so as to detect image signals from said plurality of inspection regions thus divided; measuring feature values of background levels from image signals detected at divided inspection regions adjacent to the plurality of inspection regions thus divided; and representing the image signals detected at the adjacent divided inspection regions in binary form on the basis of threshold values set based on the measured feature values, thereby detecting fine defects on the surface of the test piece based on the image signals represented in binary form.

14 Claims, 7 Drawing Sheets

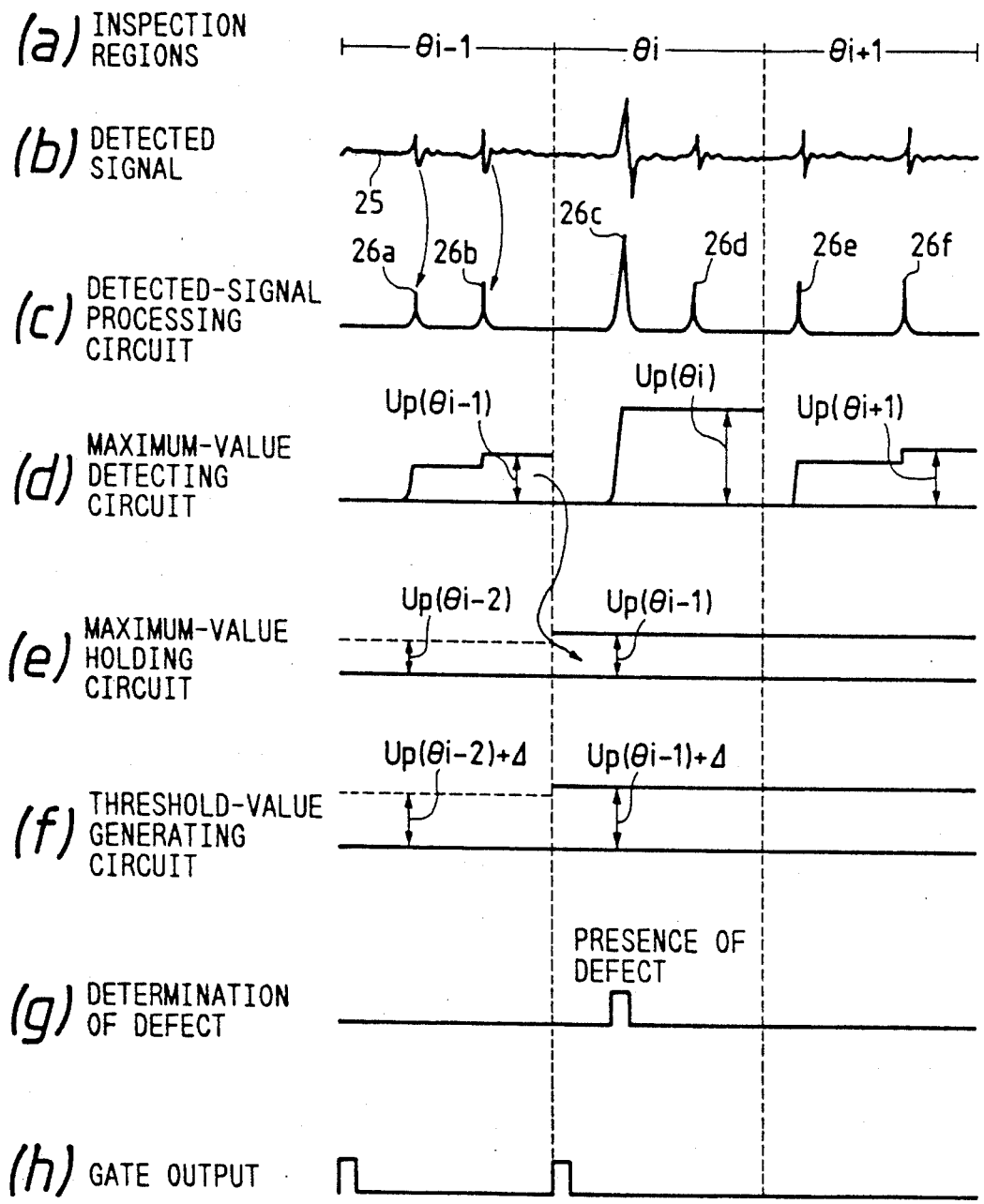

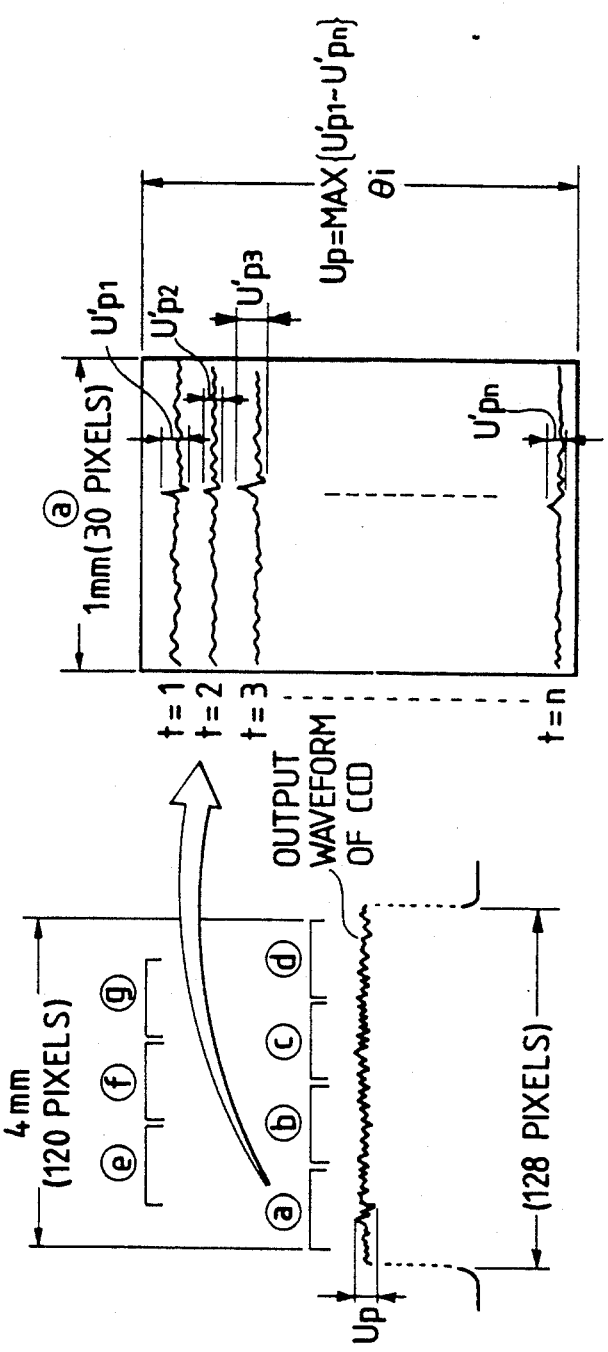
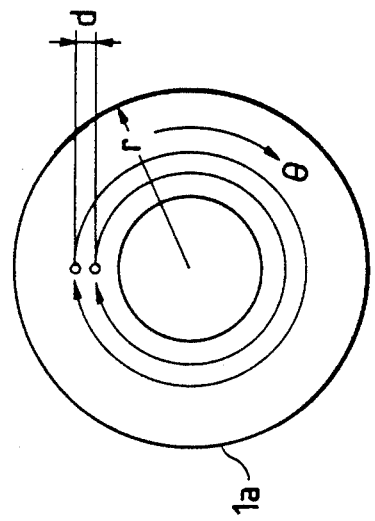
FIG. 10
FIG. 11

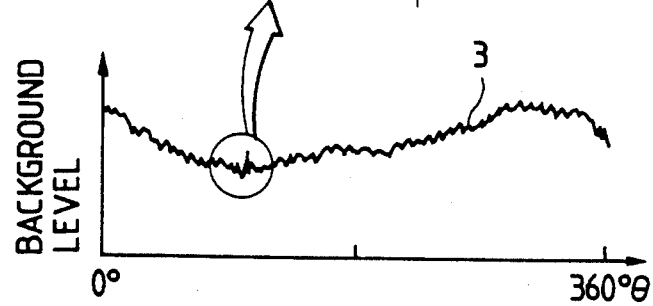
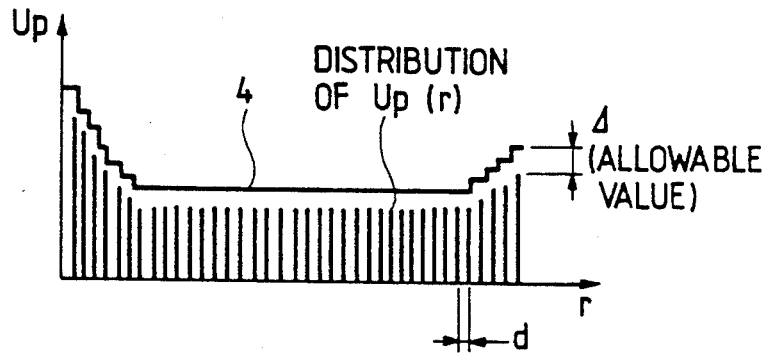
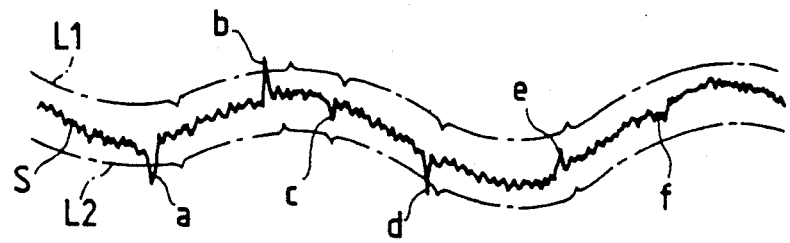

METHOD OF AND APPARATUS FOR INSPECTING SURFACE DEFECTS

BACKGROUND OF THE INVENTION

1) Field of the Invention

The present invention relates to a method of and an apparatus for inspecting defects such as flaws, projections, dust, etc. on a surface of a test piece, particularly on a coated surface of a magnetic disc.

2) Description of the Related Art

Heretofore, an inspection of a coated surface of a magnetic disc employed in a recording apparatus of a large-type computer has visually been made by an operator, for example. However, it is hard to uniformly perform its inspection due to the fact that there is a personal difference in a defect-determination criteria among operators. In recent years, it has also been difficult to visually inspect defects because the minimum dimension of a detected defect is on the order of a micron with the advancement of rendering the recording density of the magnetic disc high.

When it is desired to inspect defects such as flaws, projections, etc. present on the coated surface of the magnetic disc, for example, there is known a method in which the surface of the magnetic disc is photographically recorded by a television camera or the like so as to detect image signals, and the thus-detected image signals are represented in binary form based on threshold values, thereby recognizing defects such as the flaws, the projections on the basis of the image signals represented in binary form. When the surface to be inspected is in a stable state, such a method permits the extraction of defects by representing a detected signal from a normal surface in binary form based on a predetermined threshold value because the detected signal is constant in level.

However, when the thickness of coatings or films on the surface of the magnetic disc varies and the surface to be inspected is in an unstable state, a detected signal varies as shown in FIG. 13. When it is desired to discriminate among fine defects (a) to (b) by fixed threshold values, even a variation in a background level would be represented in binary form, thus making incapable of recognizing defects. As a method of overcoming such a drawback, there is known one of representing detected signals in binary form of a floating type as disclosed in Japanese Patent Publication Laid-Open No. 54(1979)-3638, for example.

This method is used to reduce scaled-down and smoothed signals $L_1$, $L_2$ in level from a detected signal S so as to add a predetermined level to the thus-reduced signals and subtract the same from the signals, thereby representing the results of its addition and subtraction as threshold values in binary form. According to this method, it is effective in inspecting defects on a printed-circuit board, for example. However, the method has a problem that although the defects (a), (b) and (d) can be discriminated as shown in FIG. 14 on a coated surface of a magnetic disc or the like, the defects (c) and (e) cannot be detected.

On the other hand, threshold values $L_1'$, $L_2'$ should be set as shown in FIG. 15 in order to detect even the defects (c) and (e). However, even the representation of a background level in binary form is performed as well as representation of the defects (c) and (e) in binary form in this case, thus causing a problem that false detection is performed.

In addition, a floating-threshold method is accompanied by the problem that since it makes use of dynamic response of an electric circuit, it can hardly be applied to variations in application of coatings caused in a manufacturing process as in a coated surface of a magnetic disc.

Thus, a detected signal indicative of a defect present on the coated surface of the magnetic disc is represented as shown in FIG. 12. It is hard to discriminate between the level of the detected signal and a noise level, thereby causing a problem that one fails to detect defects.

In order to solve these problems, there are known methods disclosed in Japanese Patent Publication Laid-Open Nos. 61(1986)-256242 and 62(1987)-223652.

The former discloses a method wherein a test piece such as a film of coating on a magnetic disc is scanned and recorded by photography so as to be associated with an image pick-up device, and gate signals having widths in level equivalent to dimensions of defects such as flaws, projections on a surface of the test piece are produced to be overlapped to each other, thereby making determination of the presence of a defect when the difference between the maximum and minimum values of image signals obtained from the image pick-up device within a period in which the gate signals are present exceeds a prescribed threshold value. However, the former has the problem that when a fine defect appears, it is necessary to narrow the width in level of each gate signal, thus causing difficulty in discriminating between noise components and defect components.

The latter describes a method comprising the steps of scanning and recording by photography a test piece such as a film of coating on a magnetic disc so as to be associated with an image pick-up device; producing gate signals having widths in level equivalent to dimensions of defects such as flaws, projections on a surface of the test piece to be overlapped to each other; subtracting a signal of low-frequency components out of an image signal obtained from the image pick-up device from the image signal obtained from the image pick-up device so as to determine a difference signal therebetween; integrating the difference signal over a time-width of each gate signal; and making a judgment of the presence of a defect when the value thus integrated converted into the absolute value exceeds a prescribed value.

The latter also has the problem that although a large defect can be detected in the same manner as the former, it is necessary to narrow the width in level of each gate signal in a case of presence of a fine defect, thus causing difficulty in discriminating between noise components and defect components.

As prior arts, there are known U.S. Pat. Nos. 4,674,875; 4,423,331 and 4,395,122.

SUMMARY OF THE INVENTION

It is an object of the present invention to provide a method of and an apparatus for inspecting a defect on a coated surface of a magnetic disc, the method being characterized in that fine defects such as dust, flaws, projections on the coated surface of the magnetic disc are discriminated from noise components, thereby making it possible to detect the same.

More specifically, in order to achieve the above object, there is provided a method of and an apparatus for inspecting a defect on a surface of a magnetic disc, the method comprising the steps of dividing the surface of the magnetic disc into a plurality of inspection regions; extracting feature values (noise components) from signals detected at the divided inspection regions; defining threshold values used to make a judgment of a defect at the following adjacent inspection region, using the feature values (the noise components); representing detected signals obtained at the inspection region in binary form based on the thus-defined threshold values so as to make a decision of a defect based on the detected signal represented in the binary form. In particular, when a test piece is circular as in the magnetic disc, the surface of the test piece is divided into a plurality of inspection regions along the circumferential direction thereof, thereby setting up threshold values represented in binary form at an intended inspection region on the basis of signals detected at the intended inspection region adjacent to one of the inspection regions.

Now, when it is desired to produce a magnetic disc 1, it is produced in the following manner. Namely, as shown in FIG. 8, a magnetic fluid is applied on the inner periphery of an aluminum element 40, followed by rotation of the aluminum element 40. Then, the magnetic fluid is poured into the aluminum element 40 over the regions of from the inner periphery thereof to the outer periphery thereof in the form of a concentric circle by the centrifugal force so as to apply the magnetic fluid over the entire area of the aluminum element 40, thereby forming the intended magnetic disc 1. Therefore, a magnetic material 41 applied on the aluminum element 40 becomes thicker toward the outer periphery thereof from the inner periphery thereof as shown in FIG. 8. In addition, the magnetic fluid is hardened with the elapse of time. It is therefore difficult to keep the viscosity of the magnetic fluid constant. In addition, there is produced variations in the thickness of the magnetic material 41 even in the same lot.

Thus, the magnetic material (film) 41 is formed in such a manner that it becomes thicker toward the outer periphery thereof from the inner periphery. The film 41 is semi-transparent until it is baked out and hardened. In addition, when the film 41 is subjected to radiation of scattered light, there is produced scattered light which passes through the film 41 and is reflected from a surface of the aluminum element 40 as well as scattered light reflected from a surface of the film 41 due to the fact that magnetic powder is mixed in the film 41. Namely, the scattered light reflected from the surface of the aluminum element 40 is actually detected as a background level as shown in FIG. 12. Low-frequency components of the background level are varied along the thickness of the film 41. On the other hand, local variations (noise components) $U_p$ are superposed over the background level.

It has been found out by the present inventors that the local variations $U_p$ (for each d corresponding to the radius r) show step-wise high values at portions where the radius r is smaller (the film thickness is thinner), whereas it represents step-wise high values at portions where the film thickness of the outermost periphery is thinner.

As a consequence, the present inventors found out that the local variations $U_p$ have also a relative connection with the film thickness as well as with the low-frequency components of the background level.

Thus, the present invention is particularly characterized in that the surface of the magnetic disc is divided into a plurality of inspection regions in the radial and circumferential directions (they may be overlapped at their ends), the background level is detected at the inspection region adjacent to one of the plurality of inspection regions so as to define the threshold value based on the so-detected background level, and a signal detected at the inspection region is represented in binary form based on the threshold value, thereby making it possible to detect a fine defect indicative of a variation slightly greater than the local variation $U_p$.

According to the present invention, as described above, an allowable value Δ can be reduced even when the thickness of the film of the magnetic disc varies toward a predetermined direction and variations in its thickness take place. As a result, the fine defects can be detected and the procedure for establishing the threshold values can be facilitated.

The above and other objects, features and advantages of the present invention will become apparent from the following description and the appended claims, taken in conjunction with the accompanying drawings in which a preferred embodiment of the present invention is shown by way of illustrative example.

BRIEF DESCRIPTION OF THE DRAWINGS

FIG. 7 is a diagram for describing the operation of the processing circuit shown in FIG. 6;

FIG. 10 is a diagram for describing an arithmetic procedure of $U_p$ executed in said one example shown in FIG. 9;

FIG. 11 is a diagram showing the manner in which a coated surface and the magnetic disc is scanned;

FIGS. 12A and 12B depict the level of the background reflected from the coated surface of the magnetic disc;

FIG. 13 is a diagram depicting the relationship between the radial direction and $U_p$ in the magnetic disc; and FIGS. 14 and 15 are diagrams each for describing a method of detecting defects on coated surfaces of a conventionally-known magnetic disc.

DETAILED DESCRIPTION OF THE PREFERRED EMBODIMENTS

Figure 1:
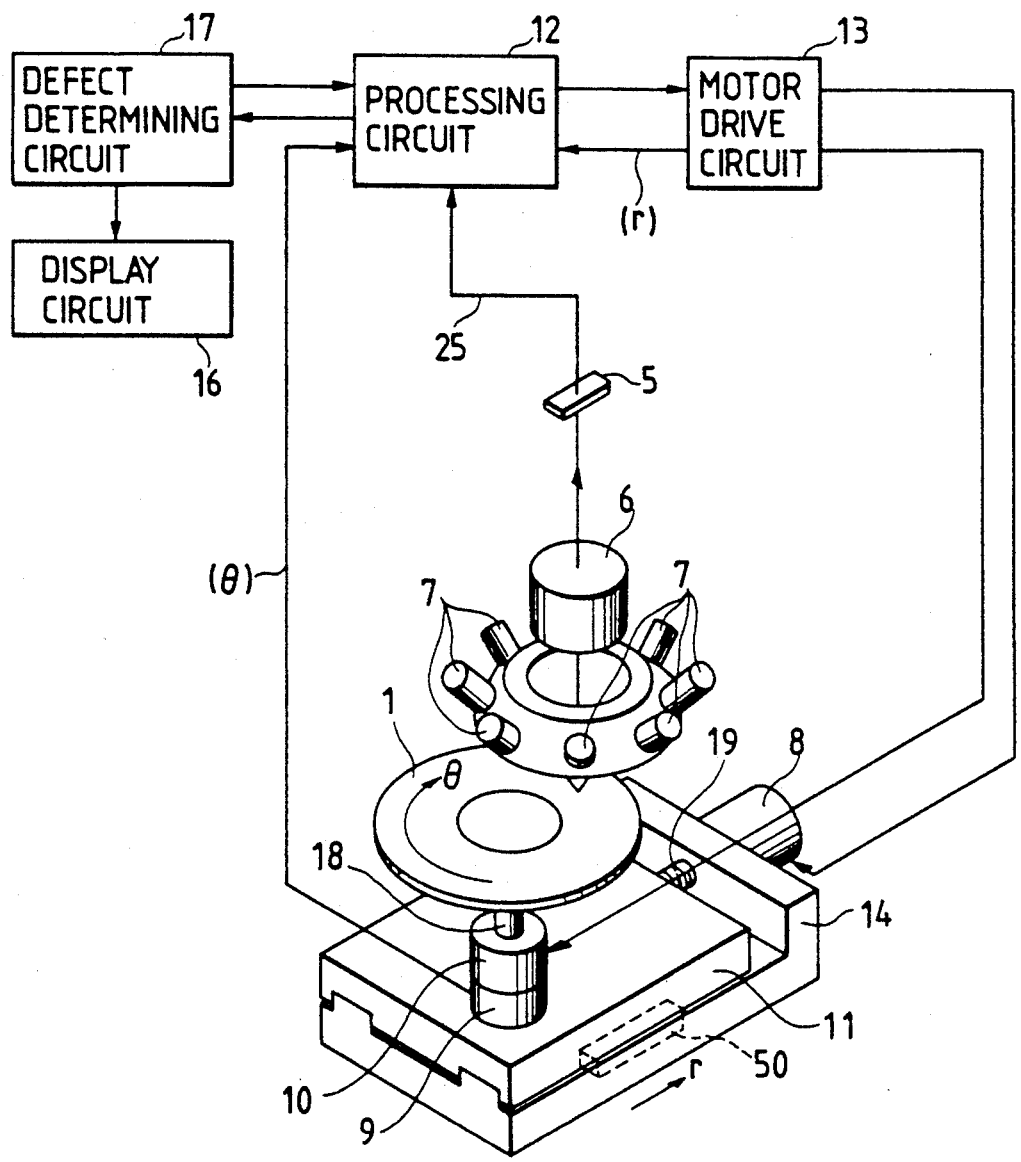
FIG. 1 is a schematic block diagram showing a surface-defect inspecting apparatus according to one embodiment of the present invention.

FIG. 1 is a diagram showing a surface-defect inspecting apparatus according to one embodiment of the present invention. In the same drawing, designated at numeral 1 is a magnetic disc formed by applying magnetic materials 41 on materials 40 made of aluminum. Designated at numerals 7 are illuminators or illuminating devices for radiating illuminating light such as white light, a laser beam to a surface of the magnetic disc 1 by diffusion from a circumferential direction to a position to be inspected. Designated at numeral 5 is a detector comprised of a CCD linear sensor, a photodiode sensor array and used to convert the intensity of received light into an electrical signal so as to output the same as a detected signal 25 therefrom. Designated at numeral 6 is a focusing lens for causing light reflected from the surface of the magnetic disc 1 to converge to the detector 5. There are further shown a base table 14, a stage 11 mounted on the base table 14 so as to be movable in a radial (r) direction of the magnetic disc 1, a feed screw 19 for moving the stage 11 in the radial direction, a motor 8 for driving the feed screw 19, a motor 10 mounted on the stage 11, a rotary encoder 9 for detecting the number of revolutions of the motor 10, and a spindle 18 attached to an output shaft of the motor 10. The magnetic disc is adsorbed on the spindle 18 by a vacuum apparatus (not shown). Furthermore, there are shown a processing circuit 12 for electrically processing the detected signal 25 from the detector 5, a motor drive circuit 13 for controlling the motors 8, 10 based on an instruction supplied from the processing circuit 12, a defect determining circuit 17 used to make a judgment or determination as to whether or not a defect exists, and a display circuit 16 for displaying the result of determination by the defect determining circuit 17.

Figure 2:
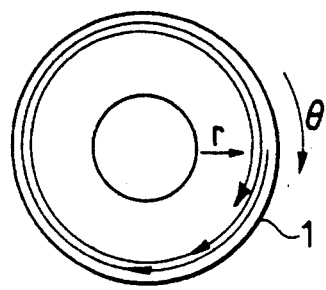
FIG. 2 is a diagram showing the manner in which a surface of a magnetic disc is scanned in the apparatus shown in FIG. 1.
Figure 3:
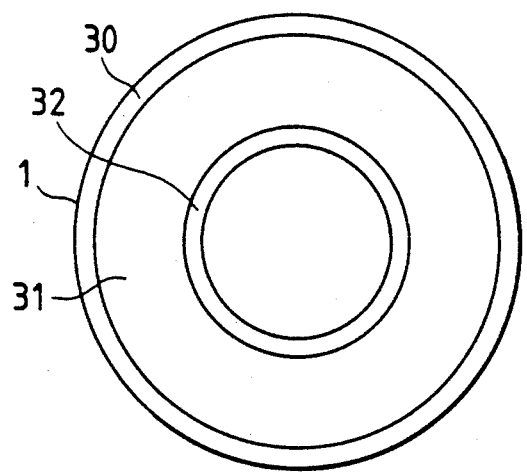
FIG. 3 is a diagram depicting an outer peripheral inspection region, an intermediate inspection region, and an inner peripheral inspection region on the magnetic disc.
Figure 4:
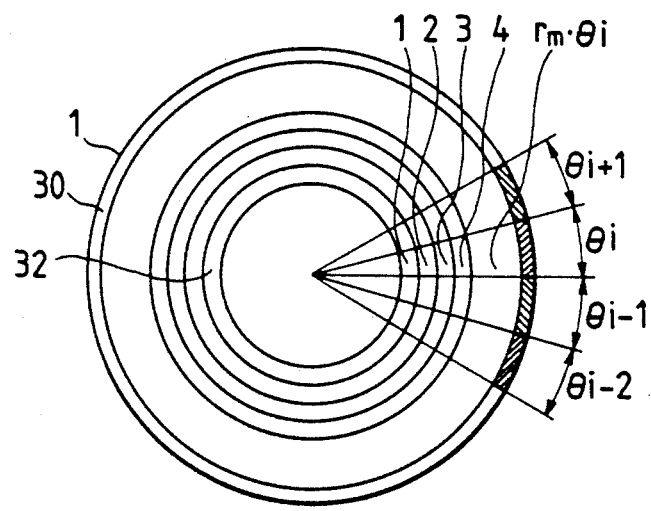
FIG. 4 is a diagram illustrating surface inspection regions of the magnetic disc, which are divided in circumferential and radial directions thereof.

In the surface-defect inspecting apparatus, the magnetic disc 1 is rotated at constant acceleration by controlling the motor 10 with the motor drive circuit 13. In addition, the motor drive circuit 13 controls the motor 8 so as to drive the feed screw 19, thereby moving the magnetic disc 1 in the radial (r) direction thereof at a constant speed. As a consequence, the surface of the magnetic disc 1 is detected in a spiral manner as shown in FIG. 2. In this case, detection is made only for the intermediate inspection region 31 shown in FIG. 3, whereas detection is made substantially one revolution over the surface of the magnetic disc 1 with respect to an outer peripheral inspection region 30 and an inner peripheral inspection region 32 without moving the stage 11. This is because of prevention of non-inspected points from being produced on the outer periphery and inner periphery. As shown in FIG. 4, inspection regions on the surface of the magnetic disc 1 are divided in the circumferential and radial directions. Then, the processing circuit 12 measures feature values [change $U_p$ in signal of maximum level, an average value (low-frequency components)] of a detected signal 25 obtained, from the detector 5, by detecting the surfaces of the thus-divided regions. Next, the feature values are used to set a threshold value used for a defect judgment at the following divided region. Thereafter, the defect determining circuit 17 compares the threshold value set by the processing circuit 12 and a value of the detected signal 25. When the value of the detected signal 25 is larger than the threshold value, the display circuit 16 display the result of presence of a defect on its screen.

In the surface-defect inspecting apparatus, feature values (change $U_p$ in signal of maximum level and an average value) of a detected signal 25 indicative of information on the surfaces of the divided regions are measured. The feature values thus measured are used so as to set a threshold value used for the defect determination at the following divided region. Therefore, an allowable value $\Delta$ can be reduced even when a thickness of film of the magnetic disc 1 varies toward a predetermined direction and variations in the thickness-of-film thereof exist, thereby making it possible to detect a fine defect. It is unnecessary to perform a process for setting the threshold value in advance by making use of a reference magnetic disc 1a. Therefore, a defect inspection work can be fabricated.

Figure 6:
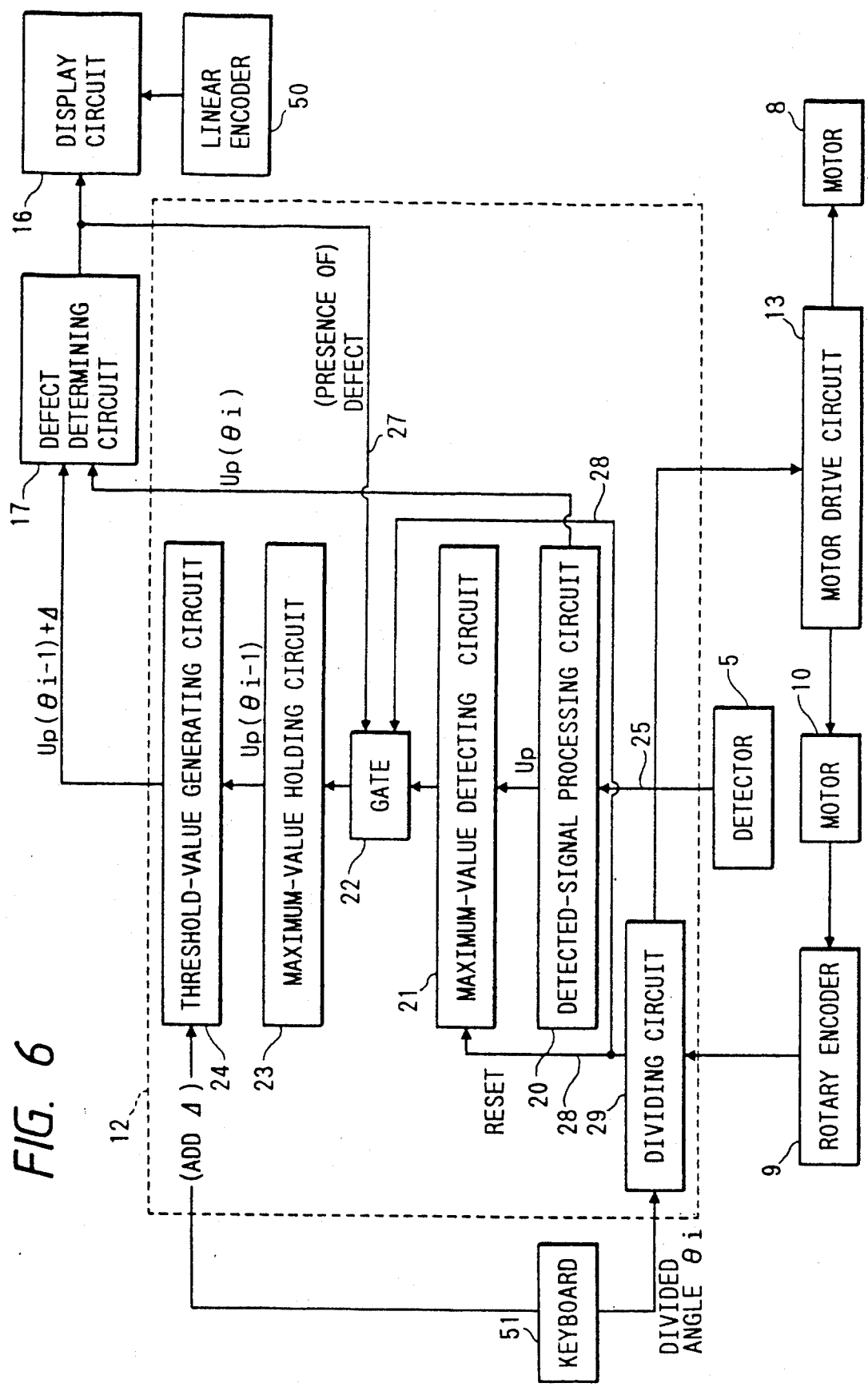
FIG. 6 is a block diagram depicting one embodiment of a processing circuit employed in the surface-defect inspecting apparatus shown in FIG. 1.
Figure 8:
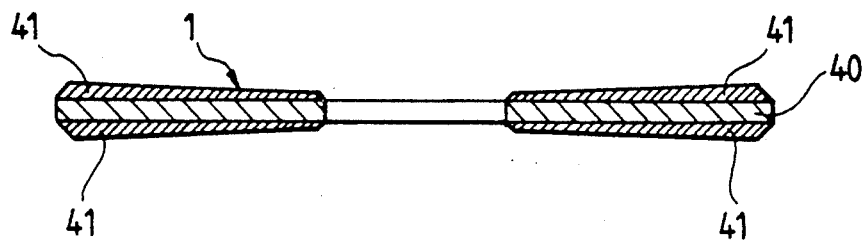
FIG. 8 is a cross-sectional view showing the magnetic disc employed in the apparatus of the present invention.

FIG. 6 is a block diagram showing one example of the surface-defect inspecting apparatus shown in FIG. 1. In the same drawing, designated at numeral 20 is a detected-signal processing circuit which outputs a peak signal 26 indicative of a local change in a detected signal 25 as shown in FIG. 7(c). Designated at numeral 29 is a dividing circuit which generates a dividing signal 28 each time a pulse of a pulse signal outputted from the rotary encoder 9 is produced at regular intervals. Designated at numeral 21 is a maximum-value detecting circuit. The maximum-value detecting circuit 21 holds the maximum peak signal 26 as shown in FIG. 7(d), and outputs the peak signal 26 held therein, i.e., the maximum-change-in-signal $U_p$ when the dividing signal 28 is inputted thereto, followed by resetting. Numeral 22 indicates a gate. As shown in FIG. 7(h), the gate 22 is kept on an ON state for a predetermined period of time starting from the time that the dividing signal 28 is inputted from the dividing circuit 29 when no signal 27 indicative of a defect is outputted from the defect determining circuit 17. On the other hand, when the defect signal 27 is outputted from the defect determining circuit 17, the gate 22 is placed on an OFF state even when the following defect signal 27 is inputted. Designated at numeral 23 is a maximum-value holding circuit which serves to hold the maximum change $U_p$ in a signal outputted from the maximum-value detecting circuit 21 until the following maximum-change-in-signal $U_p$ appears, as shown in FIG. 7(e). Designated at numeral 24 is a threshold-value generating circuit which serves to add an allowable value $\Delta$ to a value indicative of the maximum change $U_p$ in the signal outputted from the maximum-value holding circuit 23, as illustrated in FIG. 7(f).

A description will now be made of the operation of the surface-defect inspecting apparatus having such a processing circuit with reference to FIG. 7. Let's now assume that in an inspection region $\theta_{i-1}$, the output of the maximum-value holding circuit 23 is $U_p(\theta_{i-2})$, and the output of the threshold-value generating circuit 24 is $U_p(\theta_{i-2})+\Delta$, as shown in FIG. 7(f). When the detected-signal processing circuit 20 outputs peak signals 26a, 26b, the defect determining circuit 17 compares the $U_p(\theta_{i-2})+\Delta$ and each of the peak signals 26a, 26b. As a result, it is judged that each of the peak signals 26a, 26b is smaller in level than the $U_p(\theta_{i-2})+\Delta$. Therefore, the defect determining circuit 17 does not output the defect signal 27 and hence the display circuit 16 displays the absence of a defect. A description will next be made of an inspection region $\theta_i$. The maximum-value detecting circuit 21 first holds the peak signal 26a. However, the maximum-value detecting circuit 21 holds the peak signal 26b because the peak signal 26b is larger in level than the peak signal 26a. Since the defect signal 27 is not outputted from the defect determining circuit 17 in the inspection region $\theta_{i-1}$, the gate 22 is kept on the ON state for a predetermined period of time starting from the time when the dividing signal 28 is inputted from the dividing circuit 29. Therefore, the output of the maximum-value holding circuit 23 is $U_p(\theta_{i-1})$, i.e., the peak signal 26b, and the output of the threshold-value generating circuit 24 is $U_p(\theta_{i-1})+\Delta$. When the detected-signal processing circuit 20 outputs peak signals 26c, 26d, the defect determining circuit 17 compares the $U_p(\theta_{i-1})+\Delta$ and each of the peak signals 26c, 26d. As a consequence, the defect signal 27 is outputted from the defect determining circuit 17 because the peak signal 26c is larger in level than the $U_p(\theta_{i-1})+\Delta$, so that the display circuit 16 display the presence of a defect. Then, the maximum-value detecting circuit 21 holds the peak signal 26c. A description will next be made of an inspection region $\theta_{i+1}$. The defect signal 27 (indicative of the presence of a defect) is outputted from the defect determining circuit 17 in the inspection region $\theta_i$. Therefore, the gate 22 is kept on an OFF state even when the dividing signal 28 is inputted. As a consequence, the output of the maximum-value holding circuit 23 is still kept at $U_p(\theta_{i-1})$, and the output of the threshold-value generating circuit 24 is kept constant as $U_p(\theta_{i-1})+\Delta$. Thus, when the detected-signal processing circuit 20 outputs peak signals 26e, 26f, the defect determining circuit 17 compares the $U_p(\theta_{i-1})+\Delta$ and each of the peak signals 26e, 26f. As a result of its comparison, each of the peak signals 26e, 26f is smaller in level than the $U_p(\theta_{i-1})+\Delta$. Therefore, the defect determining circuit 17 does not output the defect signal 27, and hence the display circuit 16 displays the absence of a defect. The maximum-value detecting circuit 21 holds the peak signal 26f.

Figure 5:
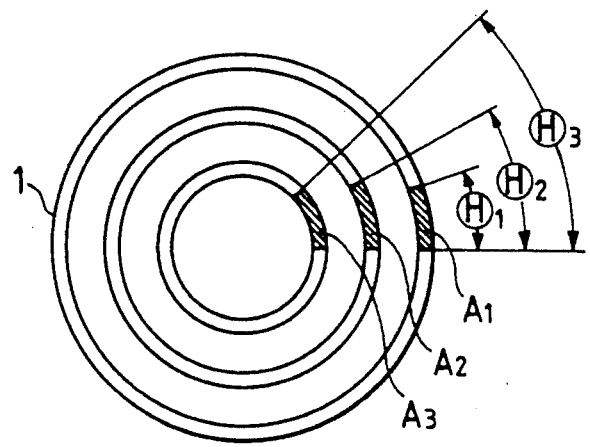
FIG. 5 is a diagram showing the manner in which areas of the surface inspection regions of the magnetic disc are divided so as to be equal to each other.

Incidentally, the inspection regions on the surface of the magnetic disc 1 are divided in the circumferential and radial directions in the above-described embodiment. However, the areas of the respective divided regions may be set equal to each other as shown in FIG. 5. In this case, the radius r of the magnetic disc 1 is inversely proportional to the angle $\Theta$ of rotation thereof, and hence $\Theta_1$ falls between $\Theta_2$ and $\Theta_3$, i.e., $\Theta_1<\Theta_2<\Theta$. The angle $\Theta$ of rotation thereof is successively set by controlling an output pulse of the rotary encoder 9 according to the number of pulses of the motor 8. In addition, a linear encoder (may be simply an encoder) 50 for detecting the amount of movement of the stage 11 is provided in the processing circuit 12. When a defect is detected while being in inspection, the linear encoder 50 outputs a coordinate signal in the radial direction of the magnetic disc 1 to the display circuit 16, and the rotary encoder 9 outputs a coordinate signal in the circumferential direction of the magnetic disc 1 to the display circuit 16. Then, if a coordinate graphic indicative of occurrence or presence of a defect is represented after completion of its inspection, the configuration of a portion indicative of a defect can be observed by an observing means such as a microscope. The control for division of the inspection regions in the circumferential direction of the magnetic disc 1 is made by counting an output pulse from the rotary encoder 9 for each predetermined number. However, the maximum value capable of being held by the maximum-value holding circuit 23 is stored in advance in the circuit 23 upon execution of an initial inspection of a first divided region at the time of a start in the inspection, and the threshold value is then set using this maximum value. At this case, when a defect exists in the following second divided region, there is a possibility of missing the defect. Therefore, inspection is made repeatedly to the first to tenth divided regions, for example, after completion of inspection of one round or revolution in the circumferential direction of the magnetic disc 1. A divided angle $\theta_i$ in the circumferential direction of the magnetic disc 1 and the allowable value $\Delta$ may arbitrarily be set externally by means of a keyboard 51 or the like. Further, the magnetic disc 1 has been subjected to one-dimensional scanning and inspected in the above-describe embodiment. However, the magnetic disc 1 may be inspected in the form of two-dimensional scanning using a CCD linear sensor, a photodiode sensor array or the like as the detector 5. In this case, if respective photodetectors are set so as to be arranged in the radial direction of the magnetic disc 1, the time required to inspect the magnetic disc 1 can be reduced. If outputs of the respective photodetectors of the detector 5 are compared with each other within tho same divided regions, in the radial direction of the magnetic disc 1 or in the circumferential direction thereof so as to determine the maximum-change-in-signal $U_p$ as described above, and the production of the threshold value and the inspection of the defect on the magnetic disc 1 are repeatedly performed, the inspection of the defect thereon can be carried out even when a defect takes place in both the radial and circumferential directions of the magnetic disc 1.

Figure 9:
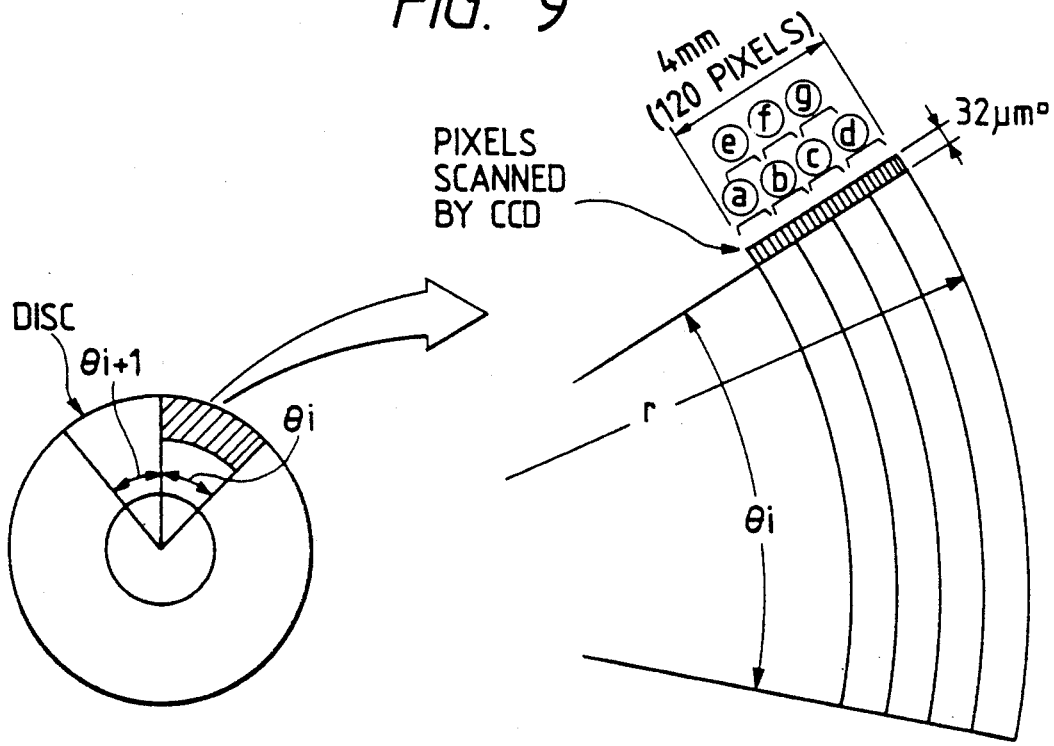
FIG. 9 is a diagram showing one example in which other inspection regions are divided in the circumferential and radial directions.

Described more specifically, there is provided an automatically threshold-value setting system of the type wherein inspection regions on the magnetic disc 1 are divided at equal intervals of $\theta_i=$about 40° in the circumferential direction of the magnetic disc 1 as shown in FIG. 9, and a change-in-signal $U_p(\theta)$ at a portion (portion of absence of a defect) where a film of coating is normal is measured for each divided region, thereby using the measured value as the threshold value. FIG. 10 shows an arithmetic sequence of $U_p$. According to the present system, the level of noise at the above normal portion of the film is measured in the inspection region $\theta_i$ for each 1 mm in the radial direction of the magnetic disc 1, thereby determining $U_p=MAX\{U'_{p-l}-U'_{pn}\}$. Respective $U_p\{(a)-(g)\}$ in the scanning direction of the CCD are measured with respect to output waveforms of the CCD linear sensor as the detector 5. The $U_p\{(e)-(g)\}$ have defects at boundaries of the $U_p\{(a)-(d)\}$, and they overlap with the $U_p\{(a)-(d)\}$ for the purpose of prevention of defects from being missed.

The CCD scans n times ($t_l$ to $t_n$) in a pitch of 32 $\mu$m over each pixel while the magnetic disc 1 being rotated $\theta_i$. Then, a change-in-signal $U'_{pt}$ (t=l-n, the maximum value of an detected output - the minimum value thereof), for each pixel, of an output signal detected by the CCD is determined for each scanning. The maximum value of $U'_p$ determined for each scanning is set as the maximum change $U_p$ in the output signal. The threshold value at the next inspection region $\theta_{i+1}$ is established by adding a constant allowable value $\Delta$ to $U_p(\theta_i)$. However, when a defect is detected at the region $\theta_i$ {when $U_p(\theta_i)>U_p(\theta_{i-1})$}, one obtained by adding the allowable value $\Delta$ to $U_p(\theta_{i-1})$ is defined as the threshold value at the region $\theta_{i+1}$.

As described above, the reason of division of respective pixels scanned by the CCD for each 1 mm in the radial direction of the magnetic disc 1 is that variations $U_p$ in noise components as well as variations in the low-frequency components is also negligible if its division is performed on the order of 1 mm or so. Thus, if the division of the pixels for each 1 mm or so in the radial direction of the magnetic disc 1 is performed, the allowable value Δ can also be set to the minimum value, thereby making it possible to detect fine defects (flaws, foreign particles, projections).

According to the surface-defect inspecting apparatus of the present invention, as has been described above, the allowable value Δ can be reduced even when the thickness of a film of a test piece is varied toward a predetermined direction and a variation in the film thickness of the test piece takes place. Therefore, the fine defects can be detected and the threshold-value setting work is unnecessary, thereby facilitating the process for the defect inspection. Accordingly, the present invention can bring about significant advantageous effects.

Having now fully described the invention, it will be apparent to those skilled in the art that many changes and modifications can be made without departing from the spirit or scope of the invention as set forth herein.

What is claimed is:

1. A method of inspecting a defect of a surface of a circular test piece, said method comprising the steps of:
   dividing the surface of the circular test piece into a plurality of inspection regions at least in a circumferential direction thereof so as to detect image signals from said plurality of inspection regions thus divided;
   detecting a maximum value of the image signal for one of the plurality of inspection regions and utilizing the detected maximum value of the one of the plurality of inspection regions to set a threshold value for enabling detection of a defect in at least an adjacent inspection region in the circumferential direction;
   detecting the image signal for the adjacent inspection region and comparing the detected image signal with the set threshold value; and
   determining a defect in the adjacent inspection region when the detected image signal exceeds the set threshold value.

2. A method according to claim 1, wherein upon determining a defect in the adjacent inspection region, detecting an image signal for a subsequent inspection region in the circumferential direction and utilizing the set threshold value for comparison.

3. A method according to claim 2, wherein when a defect is not detected in the adjacent inspection region, a maximum value of the detected image signal for the adjacent inspection region is utilized to set a new threshold value for a next adjacent region to be inspected in the circumferential direction.

4. A method according to claim 3, wherein the circular test piece is a thin film formed on a circular substrate and the detection of an image signal includes illuminating diffusion light on the surface of the circular test piece and relatively scanning the circular test piece with the diffusion light by an illumination optical system in a radial direction of the circular test piece while rotating the circular test piece and detecting a rotated displacement of the circular test piece, the step of detecting a maximum value of the image signal includes extracting a local signal change value of the image signal which is a high frequency component with respect to the image signals sequentially detected as the scanning of the circular test piece is effected.

5. A method according to claim 4, wherein the setting of the threshold value includes utilizing the detected maximum value and allowance value.

6. A method according to claim 5, wherein the step of dividing the surface of the circular test piece into a plurality of inspection regions includes dividing the surface in the circumferential direction and the radial direction wherein the inspection regions are overlapped at least in the radial direction.

7. A method according to claim 6, wherein the circular test piece is a magnetic disc and the thin film is a magnetic thin film formed on the circular substrate.

8. A method according to claim 2, wherein the circular test piece is a magnetic disc and the thin film is a magnetic thin film formed on the circular substrate.

9. Apparatus for inspecting a defect on a surface of a circular test piece, comprising:
   means for dividing the surface of the circular test piece into a plurality of inspection regions at least in a circumferential direction thereof so as to detect image signals from said plurality of inspection regions thus divided;
   means for detecting a maximum value of the image signal for one of the plurality of inspection regions and for setting a threshold utilizing the detected maximum value of the one of the plurality of inspection regions to set a threshold value for enabling detection of a defect in at least an adjacent inspection region in the circumferential direction;
   means for detecting the image signal for the adjacent inspection region and comparing the detected image signal with the set threshold value; and
   means for determining a defect in the adjacent inspection region when the detected image signal exceeds the set threshold value.

10. Apparatus according to claim 9, wherein upon determining a defect in the adjacent inspection region, the means for detecting an image signal for a subsequent inspection region in the circumferential direction utilizes the set threshold value for comparison.

11. Apparatus according to claim 10, wherein when a defect is not detected in the adjacent inspection region, the means for detecting a maximum value utilizes a maximum value of the detected image signal for the adjacent inspection region to set a new threshold value for a next adjacent region to be inspected in the circumferential direction.

12. Apparatus according to claim 11, wherein the circular test piece is a thin film formed on a circular substrate and the means for detecting the image signal includes means for illuminating diffusion light on the surface of the circular test piece and relatively scanning the circular test piece with the diffusion light by an illumination optical system in a radial direction of the circular test piece while rotating the circular test piece and for detecting a rotated displacement of the circular test piece, the means for detecting the maximum value of the image signal includes means for extracting a local signal change value of the image which is a high frequency component with respect to the image signals sequentially detected as the scanning of the circular test piece is effected.

13. Apparatus according to claim 12, wherein the means for setting a threshold value includes utilizing the detected maximum value and allowance value.

14. Apparatus according to claim 12, wherein the means for dividing the surface of the circular test piece into a plurality of inspection regions enables dividing the surface in the circumferential direction and the radial direction wherein the inspection regions are overlapped at least in the radial direction.

* * * * *